United States Patent
Hamblin, Jr. et al.

(10) Patent No.: US 6,197,054 B1
(45) Date of Patent: Mar. 6, 2001

(54) SUTURELESS CUFF FOR HEART VALVES

(75) Inventors: James Henry Hamblin, Jr., Lockhart; Billy Ray Singleton, Georgetown, both of TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/144,805

(22) Filed: Sep. 1, 1998

(51) Int. Cl.⁷ .................................................. A61F 2/24
(52) U.S. Cl. .............................................. 623/2.38; 623/2.4
(58) Field of Search ................................... 623/2, 900

(56) References Cited

U.S. PATENT DOCUMENTS

| | | |
|---|---|---|
| 3,464,065 | 9/1969 | Cromie . |
| 3,574,865 | 4/1971 | Hamaker, et al. . |
| 3,686,740 | 8/1972 | Shiley . |
| 5,397,346 | 3/1995 | Walker et al. ............................ 623/2 |
| 5,397,348 | 3/1995 | Campbell et al. ........................ 623/2 |
| 5,545,214 * | 8/1996 | Stevens ................................ 606/191 |
| 5,632,433 | 5/1997 | Grant et al. ......................... 227/179.1 |
| 5,641,111 | 6/1997 | Ahrens et al. ..................... 227/175.1 |
| 5,662,258 | 9/1997 | Knodel et al. ..................... 227/175.1 |
| 5,716,370 | 2/1998 | Williamson, IV, et al. . |

FOREIGN PATENT DOCUMENTS

| | | |
|---|---|---|
| 1504329 | 10/1967 | (FR) . |
| 1093599 | 6/1967 | (GB) . |
| WO97/30659 | 8/1997 | (WO) . |

OTHER PUBLICATIONS

Love et al., "Rapid Intraoperative Fabrication of an Autogenous Tissue Heart Valve: A New Technique", Pericardial Tissue as a Cardiac Valve Substitute, Thumersbach, Austria, pp. 691–698, Sep. 1988.*

Brochure entitled "Auto Suture Premium Plus CEEA Disposable Stapler" (1995).

* cited by examiner

Primary Examiner—David H. Willse
(74) Attorney, Agent, or Firm—Timothy L. Scott; Philip S. Lyren; Kenneth S. Barrow

(57) ABSTRACT

An improved mechanical heart valve that reduces the time required to perform heart valve replacement surgery is provided. The mechanical heart valve is comprised of a valve body and a plurality of staples extending around the valve body that are coupled to the valve body through at least one intermediate member.

34 Claims, 2 Drawing Sheets

SUTURELESS CUFF FOR HEART VALVES

BACKGROUND OF THE INVENTION

1. Field of the Invention

The present invention is directed to prosthetic heart valves, and, more particularly, to a sutureless cuff for securing a prosthetic heart valve within a patient's heart.

2. Description of the Related Art

It is well known that several heart diseases may result in a variety of disorders of the cardiac valves. For example, rheumatic fever may cause the shrinking of valve orifices. The resulting defects in heart valves hinder the normal operation of the heart. For example, defective closing of one of the valves, referred to as valvular insufficiency, may result in the accumulation of blood in the heart or regurgitation of blood past the defective valve.

To overcome these and other types of problems associated with defective heart valves, it is often necessary to completely replace the defective heart valve with a mechanical heart valve. Mechanical heart valves may come in a variety of styles and configurations. For example, a heart valve may include an annular valve body and a knit fabric sewing or suture cuff coupled to the valve body. Illustrative valves of this type are described in U.S. Pat. No. 5,397,346 entitled "Prosthetic Heart Valve With Sewing Ring" and U.S. Pat. No. 5,397,348 entitled "Mechanical Heart Valve With Compressible Stiffening Ring," both of which are hereby incorporated by reference in their entirety. In these type of mechanical heart valves, the suture cuff is sewn in place on the patient's heart tissue. Over time, the patient's heart tissue grows into the fabric to permanently seal the mechanical heart valve against leakage.

In general, heart valve replacement surgery is expensive and requires a highly-skilled team of doctors and support staff. During heart valve replacement surgery, the patient is maintained on a heart/lung bypass machine. While this procedure has worked very well, the longer the patient is on the heart/lung bypass machine, the greater the risk to the patient. It is desirable that the heart valve replacement be accomplished as quickly as possible. However, with the above-described heart valves, sewing the suture cuff to the patient's heart is time-consuming and tedious, further increasing the time that the patient is on the heart/lung bypass machine.

The present invention is directed to overcoming, or at least reducing the effects of, one or more of the problems set forth above.

SUMMARY OF THE INVENTION

The present invention is directed to a mechanical heart valve. The mechanical heart valve is comprised of a valve body and a plurality of staples extending around and fixedly attached to a first member, the first member being coupled to the valve body.

In another illustrative embodiment of the present invention, a mechanical heart valve is comprised of a valve body and a stiffening ring adapted for coupling to the valve body. The invention further comprises a backing plate that is adapted for coupling to the stiffening ring, and a plurality of staples that can be positioned on the backing plate.

BRIEF DESCRIPTION OF THE DRAWINGS

The invention may be understood by reference to the following description taken in conjunction with the accompanying drawings, in which like reference numerals identify like elements, and in which.

Figure 1:
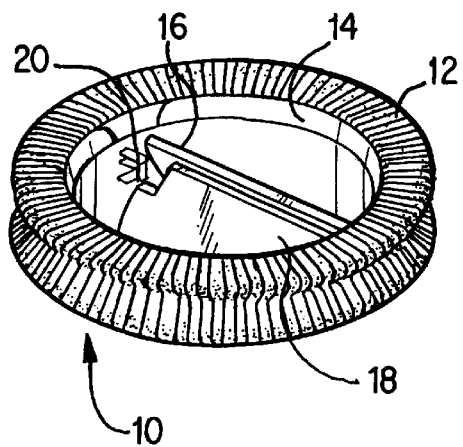
FIG. 1 is a perspective view of one embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 2:
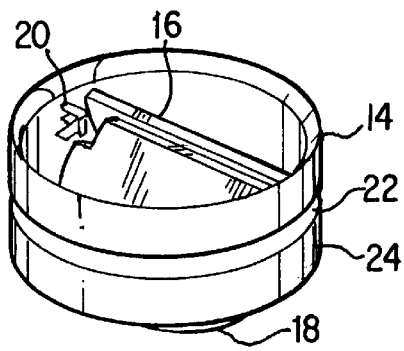
FIG. 2 is an exploded view of the device shown in FIG. 1.
Figure 2:
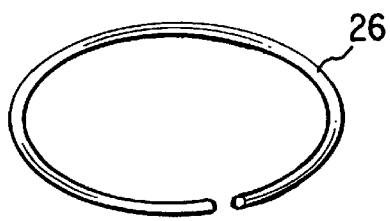
Figure 2:
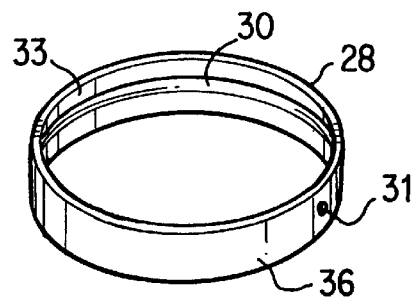
Figure 2:
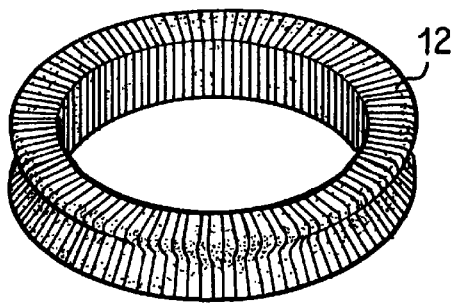

As shown in FIGS. 1 and 2, a prosthetic heart valve 10 may be comprised of an annular valve body 14, a lock wire 26, a stiffening ring 28 and a sutureless cuff 12. The valve body 14 is comprised of an outer surface 24 having an exterior groove 22 formed therein. In the illustrative embodiment disclosed herein, the heart valve 10 is comprised of two pivoting leaflets 16, 18. Of course, those skilled in the art will recognize that the heart valve 10 could be comprised of single or multiple leaflets and could even be a different type of valve, e.g., a ball valve.

The stiffening ring 28 has a like circumferential groove 30 formed in its inner surface 33 and a hole 31 that extends through the stiffening ring 28, intersecting with the groove 30. The lock wire 26 is used to couple the stiffening ring 28 to the valve body 14. In particular, the lock wire 26 may be inserted through the hole 31 into the region defined by the circumferential groove 30 on the stiffening ring 28 and the exterior groove 22 on the valve body 14. When thus inserted, the lock wire 26 prevents relative vertical movement between the stiffening ring 28 and the valve body 14.

Figure 3:
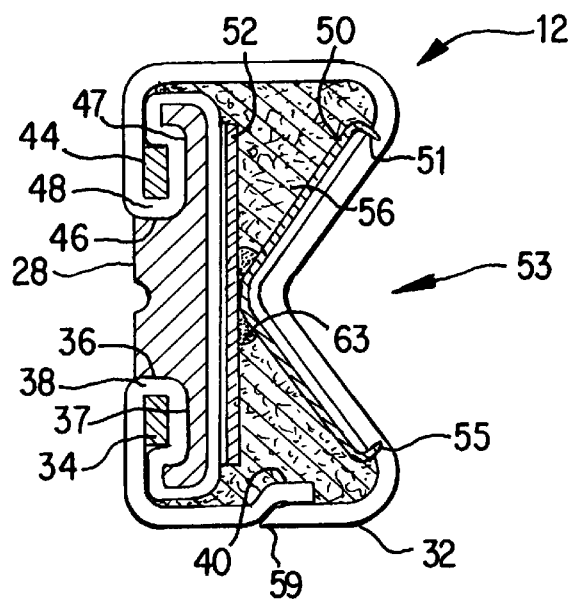
FIG. 3 is a cross-sectional view of one illustrative embodiment of the sutureless cuff of the present invention.

FIG. 3 is a cross-sectional view of one embodiment of the present invention. As shown therein, the sutureless cuff 12 may be comprised of a plurality of pre-formed staples 50, a backing plate 52, and a knit fabric tube 32. The fabric tube 32 may be coupled to the stiffening ring 28, through use of an upper capture ring 44 and a lower capture ring 34. In the illustrative embodiment shown in FIG. 3, the fabric tube 32 acts to loosely couple the combination of the backing plate 52 and staples 50 to the stiffening ring 28 and, ultimately, to the valve body 14 by use of the lock wire 26. A hole (not shown) is provided in the backing plate 52 to allow the lock wire 26 to be inserted through the hole 31 in the stiffening ring 28. Of course, those skilled in the art will recognize that a variety of different mechanical arrangements may be made that will allow the staples 50 to be coupled to the valve body 14 indirectly through one or more intermediate member, such as the stiffening ring 28 and/or the backing plate 52. For purposes of this invention, it is sufficient that the staples 50 be coupled to the valve body 14, directly or indirectly, through the use of one or more parts, such that, when the staples 50 are set, they may be used to secure the valve body 14 in the proper position in the patient's heart. Of course, this coupling of the staples 50 to the valve body 14 need not be a rigid connection.

Figure 4:
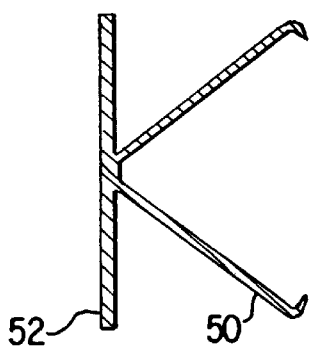
FIG. 4 is an illustrative alternative embodiment of the present invention.
Figure 5:
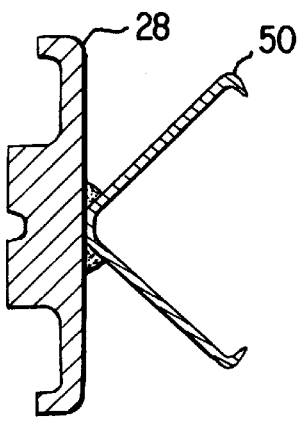
FIG. 5 is another illustrative alternative embodiment of the present invention.

The staples 50 may be coupled to the backing plate 52 by a variety of techniques, e.g., welding or forming slots in the backing plate 52. In one embodiment, the staples 50 may be attached to the backing plate 52 by, for example, welds 63. Alternatively, as shown in FIG. 4, the staples 50 may be formed integrally with the backing plate 52 to form a single unit. In another embodiment, as shown in FIG. 5, the staples 50 may be attached to the stiffening ring 28 by, for example, welding.

As shown in FIG. 3, the ends 51 and 55 of the staples 50 define a generally triangular shaped opening 53 into which will be positioned the patient's heart material. Of course, the staples 50 may be modified so as to define openings between the ends 51, 55 of the staples 50 that are other than a generally triangular cross-section. For example, the staples 50 could be configured such that the opening between the ends 51, 55 of the staple 50 define a generally rectangular or semi-circular opening. In one embodiment, the distance between the ends 51, 55 of the staple 50 may vary from approximately 0.375"–0.5". The ends 51, 55 of the staple 50 may extend radially outward from the backing plate 52 a distance that may vary in the range of approximately 0.3125"–0.375". Additionally, as those skilled in the art will recognize, the staples 50 may have a variety of cross-sectional configurations, e.g., circular, rectangular, square, etc. In one illustrative embodiment, the staples 50 have a circular cross-section of approximately 0.060 inch in diameter.

Figure 6:
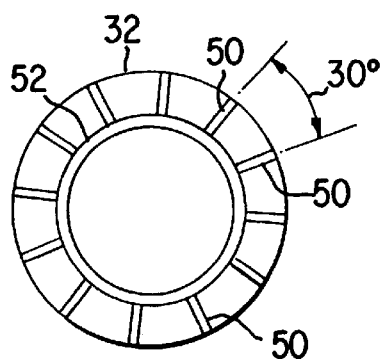
FIG. 6 is a plan view depicting one illustrative spacing arrangement of the staples that may be used with the present invention.
Figure 7:
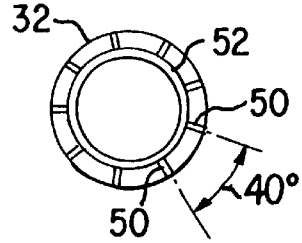
FIG. 7 is another plan view depicting one illustrative spacing arrangement of the staples that may be used with the present invention.

The size, number and location of the staples 50 positioned around the stiffening ring 28 are matters of design choice. Generally, the larger the diameter of the heart valve 10, the more staples 50 will be required. The number of staples 50 used, as well as the spacing between the staples 50, are matters of design choice. For example, for a 33 mm diameter valve, twelve of the staples 50, spaced approximately 30 degrees apart, may be positioned around the perimeter of the stiffening ring 28 as shown in FIG. 6. For a 19 mm diameter valve, nine of the staples 50, spaced at approximately 40 degrees, may be employed as shown in FIG. 7. Of course, the number and spacing of the staples 50 may be modified if desired or warranted by the particular application.

As will be readily recognized by those skilled in the art, the valve body 14, lock wire 26, stiffening ring 28, backing plate 52 and staples 50 may be manufactured from a variety of materials. In one illustrative embodiment, the valve body 14 may be made of pyrolytic carbon, a hard, wear-resistant, biocompatible material, and the lock wire 26, stiffening ring 28 and the backing plate 52 may be comprised of a biocompatible material such as titanium, cobalt-chromium, or the like. The staples 50 may be made from a variety of materials, such as, plastic or metallic materials. In one embodiment, the staples 50 may be made of stainless steel. The fabric tube 32 may be made of a variety of materials readily known to those skilled in the art. For example, the fabric tube 32 may be made of a polyester or PTFE fabric or of DACRON™ material.

The manner in which the sutureless cuff 12 may be assembled is similar to the techniques described in U.S. Pat. Nos. 5,397,346 and 5,397,348 for the assembly of the suture ring disclosed therein. U.S. Pat. Nos. 5,397,346 and 5,397,348 are hereby incorporated by reference in their entirety. The construction of the sutureless cuff 12 can be understood by reference to FIGS. 1 and 3. Construction of the sutureless cuff 12 begins with a knit fabric tube 32. The fabric tube 32 has an inner diameter that is approximately the same as the outer diameter of the stiffening ring 28. The stiffening ring 28 is placed within the fabric tube 32. The lower capture ring 34 is placed on the outside of the fabric tube 32 and pressed toward the upper edge 36 of the recess 37 formed in the stiffening ring 28. This crimps the fabric tube 32 between the stiffening ring 28 and the lower capture ring 34 at a bend 38, as seen in FIG. 3. A lower end 40 of the fabric tube 32 is wrapped downwardly around the lower capture ring 34, and the lower capture ring 34 is then pressed into the recess 37 as shown in FIG. 3. The lower end 40 of the fabric tube 32 will be attached to an upper end 59 of the fabric tube 32, as described more fully below.

After the lower capture ring 34 is positioned in the recess 37, an upper capture ring 44 is placed on the outside of the fabric tube 32 and pressed toward a lower end 46 of the recess 47 formed in the stiffening ring 28. As with the lower capture ring 34, this forms a bend 48 in the fabric tube 32 that is captured between the stiffening ring 28 and the upper capture ring 44. To complete the attachment of the sutureless cuff 12 to the stiffening ring 28, an upper end 59 of the fabric tube 32 is folded down over the staples 50 and, if used, the backing plate 52, and the upper end 59 and the lower end 40 of the fabric tube 32 are stitched together around the perimeter of the stiffening ring 28. If desired, a filler 56 such as texturized yarn, TEFLON™ felt, or molded silicon may be positioned within the fabric tube 32 adjacent the staples 50.

As is readily apparent to those skilled in the art, the sutureless cuff 12 may be assembled and attached to the valve 14 outside of the patient's body. Once properly positioned in the patient's heart, a device (not shown) may be actuated to deform the staples 50 such that the ends 51, 52 penetrate the heart material and thereby secure the valve within the heart. Thereafter, over time, the patient's heart tissue grows into the fabric providing a secure seal for the heart valve.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A mechanical heart valve comprising;
   a valve body;
   a backing plate coupled to said valve body;
   a plurality of staples for engaging a heart, said staples extending from and fixedly attached to said backing plate; and
   a cuff coupled to said valve body.

2. The mechanical heart valve of claim 1, wherein said heart valve further comprises:
   a stiffening ring coupled to said valve body;
   a plurality of capture rings engageable with said stiffening ring;
   and a lock wire engageable with said stiffening ring and said valve body,
   wherein said backing plate is coupled to said valve body by said cuff.

3. The mechanical heart valve of claim 1, wherein said heart valve further comprises:
   a stiffening ring coupled to said valve body;
   a capture ring coupling said cuff to said stiffening ring; and
   a lock wire coupling said stiffening ring and said valve body;
   wherein said cuff is positioned around at least a portion of said stiffening ring and said backing plate.

4. The mechanical heart valve of claim 1, wherein said backing plate is rigid.

5. A mechanical heart valve comprising:
   a valve body;
   a stiffening ring coupled to said valve body;
   a backing plate coupled to said stiffening ring; and
   a plurality of staples positioned on said backing plate.

6. The mechanical heart valve of claim 5, wherein said plurality of staples are attached to said backing plate.

7. The mechanical heart valve of claim 5, wherein said plurality of staples are formed integrally with said backing plate.

8. The mechanical heart valve of claim 5, further comprising a fabric material positioned around at least a portion of said backing plate and said staples.

9. The mechanical heart valve of claim 5, wherein said staples have equal radial spacings ranging from approximately 30 to 40 degrees.

10. The mechanical heart valve of claim 5, wherein said staples may vary in number from 9–12, inclusive.

11. The mechanical heart valve of claim 5, wherein said staples have a circular cross-section.

12. The mechanical heart valve of claim 5, wherein said staples have first and second ends, said first and second ends being spaced apart a distance ranging from approximately 0.375"–0.5" prior to the heart valve being installed in a patient.

13. A mechanical heart valve, comprising:
   a valve body;
   a stiffening ring adapted for coupling to said valve body; and
   a backing plate adapted for coupling to said stiffening ring, said backing plate having a perimeter and a plurality of staples attached to said backing plate, said plurality of staples extending around the perimeter of said backing plate.

14. The mechanical heart valve of claim 13, wherein said plurality of staples are equally spaced around the perimeter of said backing plate.

15. The mechanical heart valve of claim 13, further comprising a fabric material positioned around at least a portion of said stiffening ring and at least some of said staples.

16. The mechanical heart valve of claim 13, wherein said staples have equal radial spacings ranging from approximately 30 to 40 degrees.

17. The mechanical heart valve of claim 13, wherein said staples may vary in number from 9–12, inclusive.

18. The mechanical heart valve of claim 13, wherein said staples have a circular cross-section.

19. The mechanical heart valve of claim 13, wherein said staples have first and second ends, said first and second ends being spaced apart a distance ranging from approximately 0.375"–0.5" prior to the heart valve being installed in a patient.

20. A mechanical heart valve comprising:
   a valve body;
   a rigid ring coupled to said valve body, said ring having a perimeter and a plurality of staples attached to said ring and extending around the perimeter of said ring, each of said staples having a first end and a second end, said first and second ends being opposed to each other and being displaced towards each other to engage cardiac tissue.

21. The mechanical heart valve of claim 20, wherein said ring is a stiffening ring.

22. The mechanical heart valve of claim 20, wherein said plurality of staples are equally spaced around the perimeter of said ring.

23. The mechanical heart valve of claim 20, further comprising a fabric material positioned around at least a portion of said ring and at least some of said staples.

24. The mechanical heart valve of claim 20, wherein said staples have equal radial spacings ranging from approximately 30 to 40 degrees.

25. The mechanical heart valve of claim 20, wherein said staples may vary in number from 9–12, inclusive.

26. The mechanical heart valve of claim 20, wherein said staples have a circular cross-section.

27. The mechanical heart valve of claim 20, wherein, said first and second ends are spaced apart a distance ranging from approximately 0.375"–0.5" prior to the heart valve being installed in a patient.

28. A mechanical heart valve comprising:
   a valve body;
   a backing plate coupled to said valve body;
   a plurality of staples extending from and fixedly attached to said backing plate.

29. A mechanical heart valve comprising:
   a valve body;
   a lock wire;
   a stiffening ring coupled to said valve body by said lock wire; and
   a plurality of staples extending from and fixedly attached to said stiffening ring.

30. A mechanical heart valve comprising:
   a valve body,
   a rigid first member coupled to said valve body, and
   a plurality of staples extending from and fixedly attached to said first member, each of said staples having a first end and a second end, said first and second ends being opposed to each other and being displaced towards each other to engage cardiac tissue.

31. A mechanical heart valve comprising;

a valve body;

a first member coupled to said valve body;

a plurality of staples for engaging a heart, said staples extending from and fixedly attached to said first member, said first member being coupled to said valve body; each staple having a first end and a second end, said first and second ends opposing each other and being displaced towards each other to engage the heart; and a cuff coupled to said valve body.

32. The mechanical heart valve of claim 31, wherein said first member comprises a stiffening ring.

33. The mechanical heart valve of claim 32, wherein said stiffening ring is coupled to said valve body by a lock wire.

34. The mechanical heart valve of claim 31 wherein said valve body has an inflow side and an outflow side and wherein said first ends of said staples are near said inflow side before said first ends are displaced to engage the heart and said second ends of said staples are near said outflow side before said second ends are displaced to engage the heart.

* * * * *